United States Patent [19]

Izumisawa et al.

[11] Patent Number: 5,567,842

[45] Date of Patent: Oct. 22, 1996

[54] PROCESS FOR PRODUCING TEREPHTHALIC ACID

[75] Inventors: Yoshiaki Izumisawa, Tokyo; Tukasa Kawahara; Akihiko Toyosawa, both of Kitakyushu, all of Japan

[73] Assignee: Mitsubishi Chemical Corporation, Tokyo, Japan

[21] Appl. No.: 550,400

[22] Filed: Oct. 30, 1995

[30] Foreign Application Priority Data

Nov. 16, 1994 [JP] Japan .................................. 6-282178
Nov. 16, 1994 [JP] Japan .................................. 6-282179

[51] Int. Cl.$^6$ .................................................. C07C 51/43
[52] U.S. Cl. .................................................. 562/486
[58] Field of Search .................................................. 562/486

[56] References Cited

U.S. PATENT DOCUMENTS 3,931,305  1/1976  Fisher.
5,095,146  3/1992  Zeitlin .................................... 562/486

Primary Examiner—Samuel Barts

Attorney, Agent, or Firm—Oblon, Spivak, McClelland, Maier & Neustadt, P.C.

[57] ABSTRACT

A process for producing terephthalic acid, which comprises dissolving crude terephthalic acid in an aqueous medium, contacting it with a platinum group metal catalyst for purification under a temperature condition of from 260° to 320° C., crystallizing terephthalic acid from the aqueous solution of terephthalic acid by cooling the aqueous solution stepwise in a plurality of crystallizers connected in series, in such a manner that in a first crystallization zone, the crystallization temperature is adjusted to a level within a range of from 240° to 260° C. and agitating is carried out by impeller with a power requirement of impeller within a range of from 0.4 to 10 kw/m$^3$, and then, in a second crystallization zone, the crystallization temperature is adjusted to a level within a range of from 180° to 230° C., which is lower by from 20° to 60° C. than the crystallization temperature in the first crystallization zone, followed by solid-liquid separation, and drying the separated terephthalic acid crystals to obtain terephthalic acid particles wherein the proportion of particles having particle sizes exceeding 210 μm is at most 10 wt %.

17 Claims, 2 Drawing Sheets

PROCESS FOR PRODUCING TEREPHTHALIC ACID

BACKGROUND OF THE INVENTION

1. Field of the Invention

The present invention relates to a process for producing terephthalic acid. Particularly, it relates to a process for producing terephthalic acid which is suitable for use as a starting material for the production of a polyester such as polyethylene terephthalate.

2. Discussion of Background

Crude terephthalic acid obtained by oxidation of p-xylene usually contains relatively large amounts of various impurities including 4-carboxybenzaldehyde (hereinafter referred to simply as "4CBA"). Heretofore, it has been common that such terephthalic acid is purified and then used as a starting material for a polyester. As a purification method for such crude terephthalic acid, a method is common wherein crude terephthalic acid is dissolved in an aqueous medium and contacted with a platinum group metal catalyst at a high temperature under a high pressure for purification (U.S. Pat. No. 3,584,039).

Further, as a method for recovering terephthalic acid crystals after the purification reaction, a method is known wherein an aqueous solution or an aqueous slurry of terephthalic acid is cooled for crystallization stepwise in a plurality of crystallizers connected in series. For example, U.S. Pat. No. 3,931,305 discloses a method wherein cooling is carried out by setting the temperature of the crystallizer so that the precipitation rate of crystals will be smaller than in the previous step, to prevent inclusion into terephthalic acid of a p-toluic acid formed by hydrogenation of 4-carboxybenzaldehyde and thereby to maintain the purity of terephthalic acid. In this publication, there is no disclosure with respect to the relation between the various crystallization conditions and the mean particle diameter or particle size distribution of terephthalic acid crystals.

On the other hand, in recent years, it has become common to produce a polyester, particularly polyethylene terephthalate, by a so-called direct polymerization method, wherein terephthalic acid and a glycol are directly reacted. In this direct polymerization method, terephthalic acid is mixed with a glycol such as ethylene glycol to form a slurry, which is then sent to a reaction system and subjected to the reaction. In such a case, in order to increase the uniformity of the reaction, the fluidity of the slurry of terephthalic acid is desired to be excellent. Further, a good powder flowability is also required for the handling of the powder such as transportation or storage of terephthalic acid.

The fluidity of the slurry of terephthalic acid is substantially influenced by the particle size distribution or the mean particle diameter of terephthalic acid particles. Usually, the slurry properties are improved when the particle size distribution is wide with particles having large to small particle sizes, and the mean particle diameter is usually within a range of from 50 to 150 μm. If the proportion of particles having large particle sizes exceeding 200 μm increases too much, terephthalic acid tends to remain unreacted at the time of the direct polymerization, and consequently, it will be necessary to take a long reaction time, and there will be a problem such that a by-product increases.

In order to attain the uniformity of the reaction and excellent slurry properties, a large amount of a glycol may be employed relative to terephthalic acid. However, an excessive amount of glycol tends to increase a side reaction at the time of the polycondensation reaction and causes a decrease in the polymerization degree and the melting point of the polymer and even discoloration. To avoid such drawbacks, the amount of the glycol may be brought to a level as close as possible to the stoichiometric amount. However, if the amount of the glycol is decreased, it will be necessary to increase the required power for stirring the reactor and the tank for preparation of the slurry. Further, the fluidity and the reactivity of the slurry tend to be poor, and consequently there will be a problem such that the required reaction time will be long. Accordingly, terephthalic acid particles capable of forming a slurry having good fluidity and reactivity with a required minimum amount of the glycol, is most suitable as a starting material for the direct polymerization.

As a method for producing such terephthalic acid, Japanese Unexamined Patent Publication No. 29735/1973 discloses a method wherein terephthalic acid particles having a mean particle diameter of at least 100 μm and terephthalic acid particles having a mean particle diameter of at least 50 μm are mixed in a ratio of 70–85% to 30–15%. However, this method requires at least two series of crystallizing steps and is uneconomical since it requires an installation for separately storing the produced terephthalic acids, followed by mixing them again. On the other hand, Japanese Unexamined Patent Publication No. 20303/1974 discloses a method wherein recycling stirring treatment is conducted by a pump in a state of a slurry suspended in a solvent having a small solubility, so that the particle size is slightly reduced, while the apparent density is gradually improved to obtain terephthalic acid having a good slurry property. According to this method, terephthalic acid having a good slurry property can be obtained, but since the particle size is reduced, the flowability as the powder tends to be impaired, such being undesirable from the viewpoint of the handling efficiency of the powder.

Further, when multi-stage crystallization is conducted by a plurality of crystallizers, the higher the temperature in the first crystallizer is, the more the recovery efficiency of thermal energy can be improved. However, from the viewpoint of a person skilled in the art, there will be a problem that if the crystallization temperature is too high, the particle size of crystallized terephthalic acid particles tends to be too large.

SUMMARY OF THE INVENTION

It is an object of the present invention to provide a process whereby terephthalic acid particles which have a high purity and which satisfy the above-mentioned slurry property, reactivity and flowability simultaneously, can be obtained directly without requiring a complex process.

In view of the above problems, the present inventors have found it possible to industrially efficiently produce terephthalic acid particles which are highly pure and excellent in the slurry property, the powder flowability, etc. by specifying crystallization conditions for recovering terephthalic acid by multistage crystallization after purifying terephthalic acid obtained by liquid phase oxidation of p-xylene with molecular oxygen, by contacting it with hydrogen. On the basis of this discovery, the present invention has been accomplished.

Thus, the present invention provides a process for producing terephthalic acid, which comprises dissolving crude terephthalic acid in an aqueous medium, contacting it with a platinum group metal catalyst for purification under a temperature condition of from 260° to 320° C. crystallizing terephthalic acid from the aqueous solution of terephthalic acid by cooling the aqueous solution stepwise in a plurality of crystallizers connected in series, in such a manner that in a first crystallization zone, the crystallization temperature is adjusted to a level within a range of from 240° to 260° C. and agitating is carried out by impeller with a power requirement of impeller within a range of from 0.4 to 10 kw/m$^3$, and then, in a second crystallization zone, the crystallization temperature is adjusted to a level within a range of from 180° to 230° C. which is lower by from 20° to 60° C. than the crystallization temperature in the first crystallization zone, followed by solid-liquid separation, and drying the separated terephthalic acid crystals to obtain terephthalic acid particles wherein the proportion of particles having particle sizes exceeding 210 μm is at most 10 wt %.

DETAILED DESCRIPTION OF THE PREFERRED EMBODIMENTS

Figure 1:
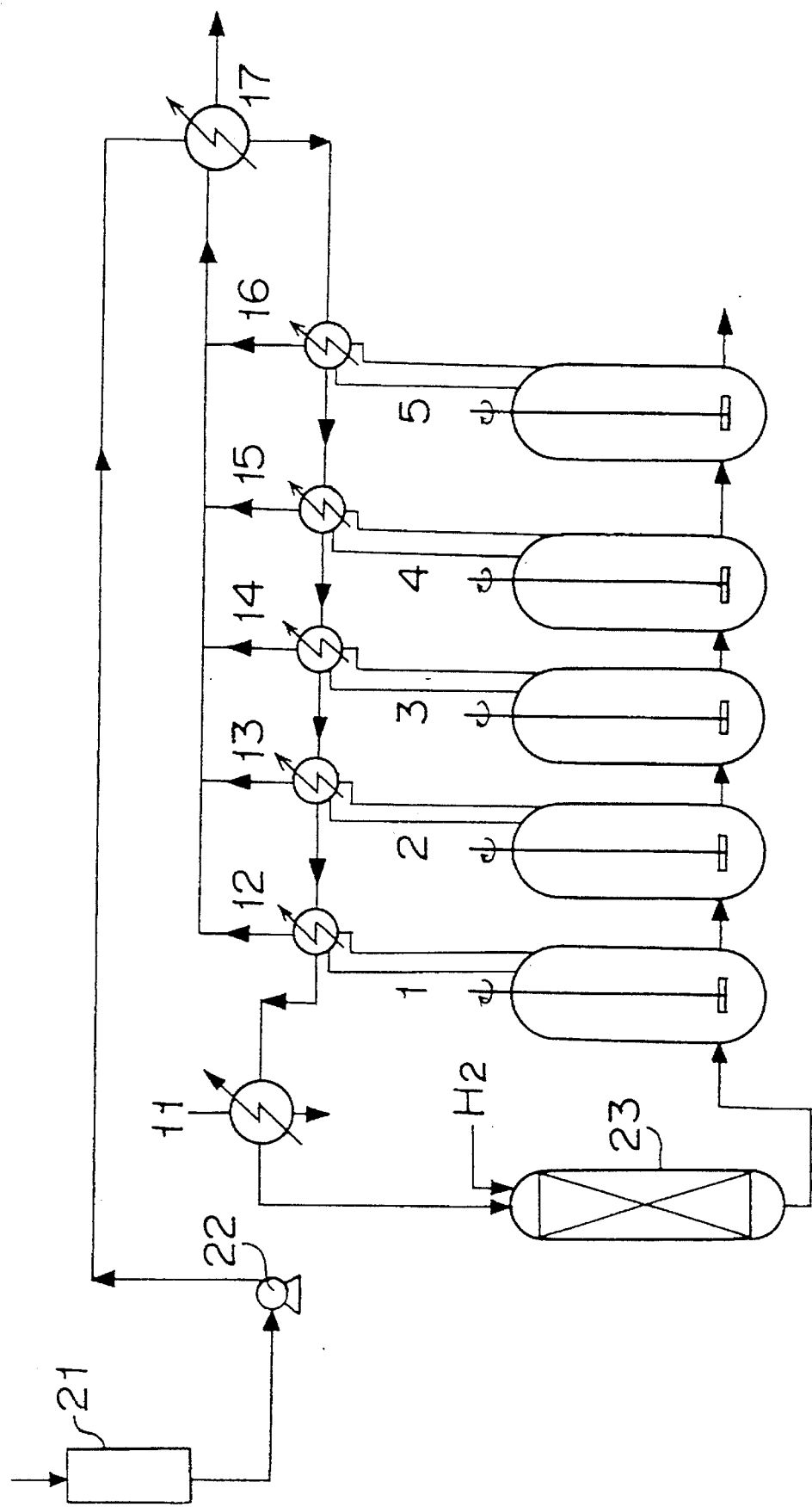
FIG. 1 is schematic view illustrating the apparatus used in Example 1.

Now, the present invention will be described in detail.

As a method for producing terephthalic acid, oxidation of p-xylene, followed by purification of an aqueous solution of crude terephthalic acid with a platinum group metal, is known. Many methods are known for such oxidation and purification. For the oxidation reaction of p-xylene, it is common to employ a method wherein p-xylene is reacted with molecular oxygen under a temperature condition of from 170° to 230° C. in an acetic acid solvent in the presence of e.g. a catalyst containing cobalt, manganese and bromine. Crude terephthalic acid obtained by this method contains 4-carboxybenzaldehyde as an impurity usually in an amount of from 500 to 10000 ppm by weight. This crude terephthalic acid is mixed with an aqueous medium to obtain a slurry usually having a concentration of from 10 to 60 wt %, preferably from 20 to 40 wt %.

Then, this slurry is pressurized by a pressurizing pump to a pressure slightly higher than the reaction pressure and sent to a heat dissolving step, whereby it is formed into an aqueous terephthalic acid solution. This aqueous terephthalic acid solution is passed through a column type reactor packed with a catalyst containing a platinum group metal. As the catalyst containing a platinum group metal, palladium, ruthenium, rhodium, osmium, iridium, platinum or the like, or an oxide of such a metal, is employed. Such a metal or a metal oxide may be used by itself as a catalyst, but may be used as supported on a carrier such as active carbon, which is insoluble in the aqueous terephthalic acid solution.

The purification of terephthalic acid by the platinum group metal catalyst can be carried out simply by contacting the aqueous terephthalic acid solution to the catalyst, but it is advantageous to conduct the purification in the presence of a reducing agent. As the reducing agent, hydrogen is usually employed. Namely, the aqueous terephthalic acid solution and hydrogen gas are supplied to a reactor and contacted to the catalyst under a temperature condition of from 260° to 320° C., preferably from 270° to 300° C. The hydrogen is supplied to the reactor usually in an amount of from 0.05 to 10 Nm$^3$ preferably from 0.1 to 3 Nm$^3$ relative to 1000 kg of the aqueous terephthalic acid solution.

The terephthalic acid from the purification step is sent to a crystallization step, where the terephthalic acid is cooled and crystallized stepwise in a plurality of crystallizers connected in series. This multi-stage crystallization is carried out by lowering the temperature stepwise by pressure release cooling in a plurality of crystallizers, usually from 2 to 7 stage, preferably from 3 to 6 stage crystallizers, connected in series, finally to a temperature at which the majority of terephthalic acid will precipitate. The formed crystals are subjected to solid-liquid separation, followed by drying to obtain terephthalic acid particles of a high purity.

In the present invention, the above multi-stage crystallization of terephthalic acid is conducted under such conditions that in the first crystallization zone, the crystallization temperature is adjusted to a level of from 240° to 260° C. and agitating is carried out by impeller with power requirement of impeller within a range of from 0.4 to 10 kw/m$^3$, and then, in the second crystallization zone, the crystallization temperature is adjusted to a level within a range of from 180° to 230° C., which is lower by from 20° to 60° C. than the crystallization temperature in the first crystallization zone. By conducting the crystallization under such a condition, it is possible to reduce the proportion of coarse particles of 200 μm or larger. Specifically, it is possible to obtain terephthalic acid particles wherein the proportion of particles having particle sizes exceeding 210 μm is at most 10 wt %.

In the crystallization of terephthalic acid in the present invention, the condition set for the first crystallization zone is most important. The temperature range in the first crystallization zone is set from 240° to 260° C., which is a high temperature region slightly lower than the purification reaction temperature of from 260° to 320° C. The first crystallization zone is usually constituted by one crystallizer. However, when a plurality of crystallizers under such a temperature range condition are to be employed, the first crystallization zone is constituted by all of such a plurality of crystallizers. In the first crystallization zone, it is preferred to crystallize most of terephthalic acid, and it is usual to crystallize at least 50%, preferably from 55 to 95%, of the total amount to be crystallized. It is conceivable to provide a preliminary crystallization zone with a temperature range exceeding 260° C. prior to the first crystallization zone set at from 240° to 260° C. However, in such a preliminary crystallization zone, the temperature is so high that the crystallization ratio is low, and accordingly, the majority of the physical properties of the crystal particles will be determined by the subsequent first crystallization zone et seq.

Here, in the multi-stage crystallization by a plurality of crystallizers, the efficiency for recovery of the heat energy may be improved as the temperature in the first crystallizer is high. However, those skilled in the art may worry that the particle sizes of crystallized terephthalic acid particles would be too large if the crystallization temperature is so high. Whereas, in the present invention, agitating impeller is provided in the crystallizer for the first crystallization zone, and agitating with sufficient power is carried out with a power requirement of impeller within a range of from 0.4 to 10 kw/m$^3$ preferably from 0.6 to 5 kw/m$^3$, whereby the particle size distribution of terephthalic acid crystal particles is adjusted so that it is possible to obtain as a final product, terephthalic acid particles wherein the proportion of particles having particle sizes exceeding 210 μm is at most 10 wt %, preferably at most 7 wt %.

Further, a large amount of steam generated by pressure release cooling of the crystallizer for the first reaction zone contains a large quantity of energy and thus can effectively be utilized as e.g. a heating energy to dissolve the crude terephthalic acid slurry. For example, steam generated in the crystallizer may directly be introduced into a heat exchanger for heating the crude terephthalic acid slurry, or steam generated in the crystallizer is heat-exchanged to generate steam which is used fop heating the crude terephthalic acid slurry. From the viewpoint of the heat efficiency or the installation efficiency, the former method is preferred. Inclusive of a case where it is preliminarily heated by a low pressure steam, the crude terephthalic acid slurry is usually gradually heated with a low temperature steam recovered from a crystallizer and with steam of the first crystallization zone, and finally heated by a heat supplied from outside to a temperature condition necessary for reduction purification of crude terephthalic acid.

The vanes of the stirrer of the crystallizer for the first crystallization zone are preferably of a type having a strong shear stress so as to bring about a change in the shape of terephthalic acid particles. For example, paddle blades, fan turbine blades, disk turbine blades, inclined fan turbine vanes or bullmergin type vanes may be mentioned. Among them, paddle blades having an angle of from 75° to 105° to the horizontal plane of the crystallizer, are particularly preferred. The rotational speed of the impeller is usually from 3 to 10 m/sec, preferably from 4 to 8 m/sec, as the speed of the forward ends of the impeller. When the inner diameter of the crystallizer is D, the diameter of the impeller is usually within a range of from 0.2D to 0.7D, preferably from 0.3D to 0.6D. Further, to provide impact plates in the vicinity of the impeller in the crystallizer may sometimes be effective to reduce the load of the agitating power and to efficiently obtain desired terephthalic acid particles, although such is not an essential requirement. Such impact plates are particularly effective when they are disposed with a distance of from 0.01 to 0.1D from the forward ends of the impeller. These impact plates are different from usual baffle plates, and they are usually disposed with a distance from the inner wall of the crystallizer. The impact plates are fixed to the crystallizer, but there is a distance between the impact plates and the inner wall, so that the slurry current in the crystallizer can freely flow through the space.

The impact plates are preferably disposed on an extended line of the rotational radius of the impeller, i.e. on the straight line connecting the rotational shaft of the agitator and the inner wall of the crystallizer. However, they may be disposed in a direction departing form this straight line more or less, so long as the function that the slurry current formed by the impeller will collide thereto, will not be impaired. The width of the impact plates i.e. the length along the direction of the above disposition is preferably within a range of from 0.05D to 0.2D. If this width is too wide, the flow of the slurry current formed by the impeller will be substantially hindered, whereby local non-uniformity will be brought about. On the other hand, if the width is too small, the effects tend to be small.

The height of the impact plates (the length in the longitudinal direction) is preferably at least the height of the impeller. It is usually preferred that the upper edge of the impact plates is on the same horizontal line as the upper edge of the impeller blades or above such a horizontal line. Likewise, the lower edge of the impact plates is preferably on the same horizontal line as the lower edge of the impeller blades or below such a horizontal line. When the height and disposition of the impact plates are so adjusted in the relative relation with the impeller, the function of the impact plates such that the slurry current formed by the impeller collides against them, can be fully obtained.

In a case where impeller is attached in multi-stages on the agitating shaft, it is necessary to provide impact plates so that they correspond at least to the impeller of the lowest stage. Impact plates may or may not be provided in the vicinity of the impeller provided above the lowest stage impeller. If such additional impact plates are provided, they may be formed integral with the impact plates provided in correspondence with the impeller of the lowest stage, i.e. they may have a shape such that the impact plates of the lowest stage are extended upward. The number of impact plates is usually from 2 to 20 plates, preferably from 4 to 12 plates, which are preferably disposed with substantially the same distances. As mentioned above, the impact plates are different from usual baffle plates. Accordingly, in addition to the impact plates, baffle plate may be provided on the inner wall of the crystallizer by a usual method, to improve the stirring and mixing of the slurry in the crystallizer, as the case requires.

In addition to the above-mentioned crystallization condition for the first crystallization zone, the crystallization condition for the second crystallization zone is also an important requirement in the present invention. Namely, in the second crystallization zone, the crystallization temperature is required to be adjusted to a level of from 180° to 230° C., preferably from 185° to 225° C., and the crystallization temperature is required to be lower by from 20° to 60° C., preferably from 25° to 55° C., than the crystallization temperature in the first crystallization zone. If the crystallization temperature in the first crystallization zone is lower than 240° C. the mean particle diameter tends to be small, and the particle shape tends to be distorted, such being undesirable. By increasing the crystallization temperature in the first crystallization zone, the mean particle diameter increases, and the particle shape tends to be round, whereby the powder property as a terephthalic acid product will be good. However, if the proportion of large particles is too much, the reactivity of the product may sometimes become poor.

Therefore, the mean particle diameter of terephthalic acid particles is usually desired to be from 50 to 150 μm, preferably from 70 to 130 μm. By conducting crystallization under the above condition in the second crystallization zone, it is possible to increase the proportion of fine particles having particle sizes of less than about 50 μm, while maintaining the mean particle diameter within the above range, in the particle size distribution of terephthalic acid particles, whereby the slurry property as a terephthalic acid product will be good. To adjust such a particle size distribution of terephthalic acid particles to an appropriate condition, it is necessary to provide a certain temperature difference between the first crystallization zone and the second crystallization zone. If this temperature difference becomes too large, the particle size reduction proceeds too much, whereby the means particle diameter tends to be so small that slurring will be difficult, or an impurity such as paratoluic acid is likely to be included in terephthalic acid particles, thus leading to a problem from the viewpoint of the product quality.

If necessary, third or further crystallization zones may be provided for further cooling for crystallization. In such a case, a method may, for example, be mentioned in which a plurality of crystallizers are sequentially cooled with substantially the same temperature difference usually in from 2 to 7 stages, preferably in 3 to 5 stages, usually from 170° to 80° C. Also in the second crystallizer et seq, impeller is usually provided, but agitating is not particularly restricted to the condition as defined for the first crystallizer, and the power requirement of impeller is usually from 0.2 to 3 kw/m³, the speed of the forward ends of impeller blades is usually from 1 to 10 m/s, and there is no particular restriction as to the shape and size of vanes. Then, formed crystals of terephthalic acid are subjected to solid-liquid separation, followed by drying to obtain terephthalic acid particles of a high purity. The terephthalic acid particles thus obtained by the present invention can be suitably used by itself as a starting material for a polyester.

According to the study by the present inventors, it has been found that when terephthalic acid is used as a starting material for the polyester, a very small amount of bulky particles having a particle size of a few mm e.g. a particle size within a range of from 1 to 5 mm, in the terephthalic acid particles, which have been heretofore almost neglected, sometimes gives a substantial influence over the process for production of the polyester or the product quality.

Accordingly, when used as a starting material for a polyester, the terephthalic acid particles of the present invention are desired to contain bulky particles as little as possible, and usually bulky particles of terephthalic acid having particle sizes exceeding 2.0 mm are preferably at most 0.5 ppm, more preferably at most 0.3 ppm. Further, bulky particles of terephthalic acid having particle sizes exceeding 1.0 mm are preferably at most 20 ppm, more preferably at most 10 ppm.

The above-mentioned bulky particles are unavoidably formed in a very small amount in the process for producing terephthalic acid. Such bulky particles of terephthalic acid may include those peeled off from scales in the reactor, crystallizers and pipes in various steps and those formed by disintegration or peeling of solid products in the separator for terephthalic acid particles, the conveyor for transportation, the dryer, etc. as well as those formed by solidification of particles during the storage in e.g. a silo. Such bulky particles tend to contain colored impurities or foreign matters such as metal components, and in the esterification step, dissolution of the bulky particles of terephthalic acid is slow, and they tend to remain as a solid, whereby they tend to cause clogging of a filter in the polymerization step or in the transportation step to the step of polymerization of the esterified oligomer. Further, if bulky particles remain, they are considered to cause color shading in the polyester product, reduction of heat resistance or thread breakage during spinning.

Accordingly, it is desired to prevent formation of such bulky particles in the process for production of terephthalic acid, and a method for preventing formation of bulky particles is conceivable such as reviewing the production conditions such as the temperatures and drying states of the systems or periodical cleaning of the systems. By controlling formation of bulky particles to the minimum level, it is possible to reduce also bulky particles which can not be removed by the above-mentioned sieve.

However, in order to obtain terephthalic acid containing little bulky particles constantly for a long period of time, it is advisable to provide a step for removing bulky particles. There is no particular restriction as to the method for removing bulky particles in the terephthalic acid particles. However, it is conceivable to employ a method for removing bulky particles of a size larger than a specified level by providing a sieve at any one or every one of a plurality of places such as the outlet of the dryer in the process for producing terephthalic acid, the outlet of the product silo, and the inlet of a discharge hopper. For example, by using a sieve with an opening size of about 2 mm, bulky particles having sizes of about 2 mm or larger may be removed. Further, it is preferred to remove bulky particles having a maximum length of about 1 mm or longer by using a sieve having an opening size of about 1 mm. However, a substantial installation load is industrially expected for the treatment by means of such a sieve having an opening size of about 1 mm.

Now, the present invention will be described in further detail with reference to Examples. However, it should be understood that the present invention is by no means restricted to such specific Examples.

EXAMPLE 1

A 30 wt % aqueous slurry of crude terephthalic acid obtained by oxidizing p-xylene with molecular oxygen in an acetic acid solvent in the presence of cobalt, manganese and bromine compounds, was prepared, and the slurry was pressurized, supplied at a predetermined flow rate to a heater and dissolved. The solution was introduced into a column type reactor packed with a Pd/C catalyst, and hydrogen was supplied at a predetermined flow rate, followed by hydrogenation reaction at a reaction temperature of 290° C. under a reaction pressure of 9MP. With respect to the aqueous terephthalic acid solution subjected to the hydrogenation reaction treatment, crystallization of terephthalic acid was carried out stepwise by evaporation cooling of the water solvent by means of an apparatus having five crystallizers of the same capacity connected in series. FIG. 1 shows a schematic view illustrating the apparatus used in Example 1. In FIG. 1, reference numerals 1 to 5 indicate the respective crystallizers, numerals 11 to 17 heat exchangers, numeral 21 a slurry preparation tank, numeral 22 a pressurizing pump, and numeral 23 a hydrogenation reactor.

Here, as the first crystallizer, the inner diameter D of the crystallizer was 3.6 m, five baffle plates with a distance of 0.1D from the inner wall of the crystallizer were disposed at the same distance from one another, and an agitator of a rotational speed-changeable type having agitating impeller 25 of a vertical paddle type with four vanes (vane diameter d: 0.36D, blade width c: 0.13D) was employed. For the second to fifth crystallizers, an agitator having impeller of downwardly driving type with four blades of 45° inclination (impeller diameter: 0.42D), was used at a constant rotational speed of 60 rpm (power requirement of impeller: 0.7 kg/m³, speed of the forward ends of impeller: 4.7 m/s). The first crystallizer was maintained at 252° C., whereby about 70% of the total amount of crystallization was crystallized. In the second crystallizer et seq, the temperature was gradually lowered, and the fifth crystallizer was set at a temperature of about 150° C. Here, the residence time in each crystallizer was set to be about 20 minutes. The formed terephthalic acid slurry was continuously withdrawn from the fifth crystallizer, and while maintaining the crystallization temperature, crystal particles of terephthalic acid were centrifugally separated and dried.

Table 1 shows the main conditions in the above crystallization and the results of the physical property test of the purified terephthalic acid particles. In Table 1, the particle size distribution is the value measured by wet screening with JIS standard sieves, and the mean particle diameter is the diameter corresponding to a weight accumulation of 50%. The slurry torque is the stirring torque when a slurry having 1.1 mols of ethylene glycol mixed to 1 mol of terephthalic acid, was stirred by a two blades impeller at 25° C. The powder discharge property is represented by the time required for discharging 300 g of terephthalic acid particles under a predetermined vibration condition from a hopper having an opening of 64 mm². The slurry torque is, of course, desired to be as small as possible. The powder discharge property is desired to be usually at most 150 seconds, and if it exceeds 150 seconds, the flowability of the powder is extremely poor. With respect to the particle size distribution, if coarse particles exceeding 200 μm increase, the reactivity tends to be poor.

Further, with respect to the energy in the large amount of steam generated by pressure release cooling of the crystallizer in each crystallization zone, the steam generated in each crystallizer, was directly introduced into an exchanger tube for heating the crude terephthalic acid slurry. With respect to the crude terephthalic acid slurry, the quantity of energy required for heating subsequent to the heat exchange with the steam of the first crystallizer, was 330 MJ/ton slurry in Example 1, whereas it was 420 MJ/ton slurry in Comparative Example 2 given hereinafter.

EXAMPLES 2 to 5 and COMPARATIVE EXAMPLES 1 and 2

In Example 1, the crystallization conditions in the first and second crystallizers were changed as shown in Table 1, and the results are shown in Table 1.

forward ends of vanes: 4.4 m/sec). The results of crystallization under various conditions are shown in Table 2. In Table 2, in Comparative Example 3, slurrying was impossible, whereby it was impossible to measure the slurry torque.

In the second and subsequent crystallizers, the temperature was sequentially lowered, and the fifth crystallizer was about 150° C. Here, the residence time in each crystallizer was about 30 minutes. The formed terephthalic acid slurry was continuously withdrawn from the fifth crystallizer, and while maintaining the crystallization temperature, the crystal particles of terephthalic acid were centrifugally separated and dried.

COMPARATIVE EXAMPLES 6 and 7

In Example 6, also used in the first crystallizer was the same agitator having impeller of a downwardly driving type with four blades of 45° inclination (vane diameter: 0.45D) as used in the second to fifth crystallizers, and the results are shown in Table 2.

TABLE 1

|  |  | Ex. 1 | Ex. 2 | Ex. 3 | Ex. 4 | Ex. 5 | Comp. Ex. 1 | Comp. Ex. 2 |
|---|---|---|---|---|---|---|---|---|
| First crystallizer | Temperature (°C.) | 252 | 252 | 242 | 247 | 247 | 252 | 237 |
|  | Peripheral speed of impeller (m/s) | 6.1 | 4.8 | 6.1 | 6.1 | 6.1 | 3.7 | 6.1 |
|  | Power (kw/m³) | 1.6 | 0.7 | 1.6 | 1.6 | 1.6 | 0.3 | 1.6 |
| Second crystallizer temperature (°C.) |  | 219 | 219 | 213 | 213 | 221 | 219 | 213 |
| Particle size distribution | 210 μm< | 4% | 5% | 2% | 3% | 4% | 12% | 1% |
|  | 177–210 | 3 | 7 | 4 | 6 | 6 | 8 | 3 |
|  | 149–177 | 12 | 10 | 8 | 10 | 11 | 9 | 6 |
|  | 105–149 | 23 | 21 | 22 | 23 | 24 | 16 | 21 |
|  | 74–105 | 21 | 17 | 22 | 18 | 19 | 13 | 21 |
|  | 44–74 | 14 | 12 | 17 | 18 | 19 | 10 | 15 |
|  | 44 μm> | 23 | 28 | 25 | 22 | 17 | 32 | 34 |
| Mean particle diameter (μm) |  | 94 | 92 | 86 | 91 | 97 | 94 | 75 |
| Slurry torque (g · cm) |  | 180 | 170 | 220 | 170 | 200 | 180 | 270 |
| Powder discharge property (sec) |  | 90 | 100 | 120 | 90 | 90 | 180 | 180 |

EXAMPLES 6 to 8 and COMPARATIVE EXAMPLES 3 to 5

Figure 2:
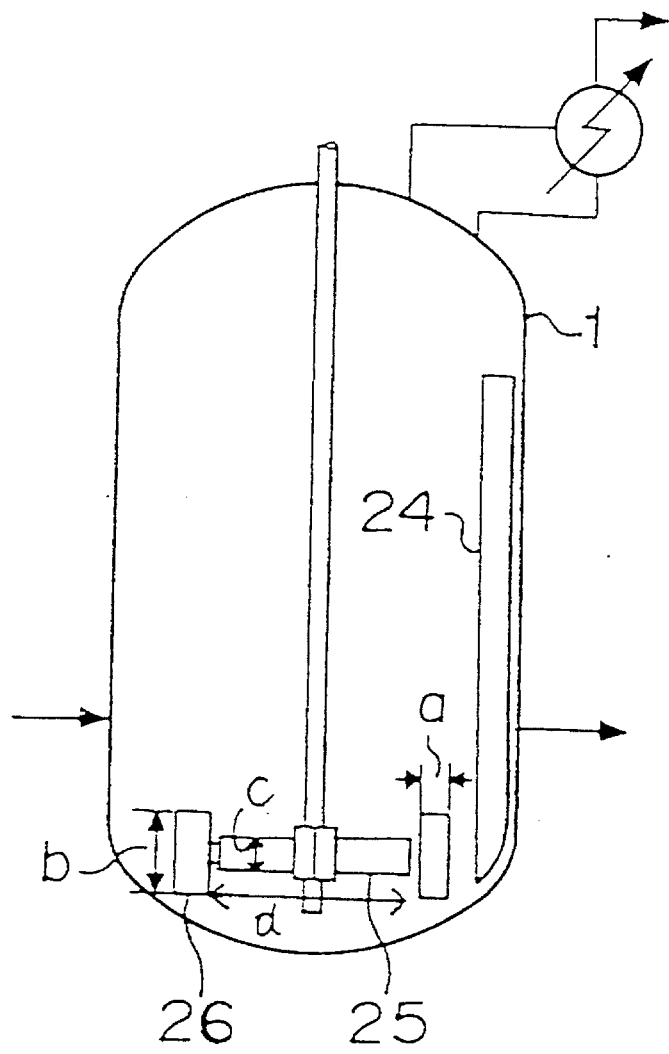
FIG. 2 is a schematic view illustrating the first crystallizer used in Example 6.

As the first crystallizer, the one as shown in FIG. 2 was used, wherein the inner diameter D of the crystallizer was 3.1 m, five baffle plates 24 with a distance of 0.1D from the inner wall of the crystallizer were provided at the same distance from one another, and ten impact plates 26 having a width a of 0.1D and a height b which was twice the width of the impeller blades 25, were provided at an equal distance with a space of 0.03D from the forward ends of impeller 25, on a straight line connecting the center axis of the crystallizer and inner wall of the crystallizer. Further, an agitator of a rotational speed-changeable type having impeller of a vertical paddle type with four vanes (impeller diameter d: 0.36D, vane width c: 0.13D), was used. For the second to fifth crystallizers, a stirrer having stirring vanes of a downwardly driving type with four blades of 45° inclination (impeller diameter: 0.45D) was used at a constant rotational speed of 60 rpm (agitating power: 0.5 kg/m³, speed of the

TABLE 2

|  |  | Ex. 6 | Ex. 7 | Ex. 8 | Comp. Ex. 3 | Comp. Ex. 4 | Comp. Ex. 5 | Comp. Ex. 6 | Comp. Ex. 6 |
|---|---|---|---|---|---|---|---|---|---|
| First crystallizer | Temperature (°C.) | 244 | 244 | 253 | 244 | 244 | 234 | 231 | 242 |
|  | Peripheral speed of impeller (m/s) | 5.6 | 4.9 | 5.6 | 5.6 | 5.6 | 5.6 | 4.4 | 4.4 |
|  | Power (kw/m³) | 1.3 | 0.7 | 1.3 | 1.3 | 1.3 | 1.3 | 0.5 | 0.5 |
| Second crystallizer temperature (°C.) |  | 200 | 200 | 200 | 180 | 230 | 200 | 200 | 212 |
| Particle size distribution | 210 μm< | 4% | 6% | 6% | 1% | 6% | 0% | 4% | 18% |
|  | 177–210 | 7 | 9 | 7 | 3 | 8 | 2 | 9 | 12 |
|  | 149–177 | 10 | 9 | 10 | 8 | 15 | 4 | 10 | 13 |
|  | 105–149 | 23 | 22 | 22 | 12 | 38 | 24 | 25 | 20 |
|  | 74–105 | 18 | 17 | 13 | 14 | 13 | 12 | 18 | 14 |
|  | 44–74 | 17 | 19 | 11 | 21 | 12 | 28 | 17 | 12 |
|  | 44 μm> | 21 | 18 | 31 | 41 | 8 | 30 | 17 | 11 |
| Mean particle diameter (μm) |  | 95 | 98 | 94 | 55 | 128 | 64 | 102 | 103 |
| Slurry torque (g · cm) |  | 160 | 200 | 150 | ** | 280 | 390 | 290 | 160 |
| Powder discharge property (sec) |  | 120 | 90 | 140 | >200 | 90 | 130 | 90 | 60 |

**: Not measurable

According to the present invention, it is possible to obtain terephthalic acid of a high purity excellent in the slurry property, the reactivity, the powder flowability, etc. and suitable for use for production of a polyester. Further, when the present invention is employed, efficient recovery of heat energy generated in the system for production of terephthalic acid, is easy.

What is claimed is:

1. A process for producing terephthalic acid, which comprises dissolving crude terephthalic acid in an aqueous medium, contacting it with a platinum group metal catalyst for purification under a temperature condition of from 260° to 320° C., crystallizing terephthalic acid from the aqueous solution of terephthalic acid by cooling the aqueous solution stepwise in a plurality of crystallizers connected in series, in such a manner that in a first crystallization zone, the crystallization temperature is adjusted to a level within a range of from 240° to 260° C. and agitating is carried out by impeller with a power requirement of impeller within a range of from 0.4 to 10 kw/m³ and then in a second crystallization zone, the crystallization temperature is adjusted to a level within a range of from 180° to 230° C., which is lower by from 20° to 60° C. than the crystallization temperature in the first crystallization zone, followed by solid-liquid separation, and drying the separated terephthalic acid crystals to obtain terephthalic acid particles wherein the proportion of particles having particle sizes exceeding 210 μm is at most 10 wt %.

2. The process according to claim 1, wherein the crude terephthalic acid is dissolved in the aqueous medium at a concentration of from 10 to 60 wt %, followed by contacting with the platinum group metal catalyst for purification.

3. The process according to claim 1, wherein the crystallization ratio in the first crystallization zone is from 55 to 95%.

4. The process according to claim 1, wherein the agitating is carried out by impeller of a crystallizer for the first crystallization zone with a power requirement of impeller within a range of from 0.6 to 5 kw/m³.

5. The process according to claim 1, wherein the peripheral speed of forward ends of the impeller of a crystallizer for the first crystallization zone, is from 3 to 10 m/sec.

6. The process according to claim 1, wherein the peripheral speed of forward ends of the stirring vanes of a crystallizer for the first crystallization zone, is from 4 to 8 m/sec.

7. The process according to claim 1, wherein the impeller of a crystallizer for the first crystallization zone are paddle blades having an angle of 75° to 105° to the horizontal plane of the crystallizer.

8. The process according to claim 1, wherein, when the inner diameter of a crystallizer for the first crystallization zone is D, the impeller diameter is from 0.2 to 0.7D, a plurality of impact plates having a width of from 0.05 to 0.2D are disposed in a longitudinal direction with a distance of from 0.01 to 0.1D from the forward ends of the impeller blade.

9. The process according to claim 1, wherein in the second crystallization zone, the crystallization temperature is adjusted to a level within a range of from 185° to 225° C., which is lower by from 25° to 55° C. than the crystallization temperature in the first crystallization zone.

10. The process according to claim 1, wherein from 3 to 7 crystallizers connected in series, are employed, and the aqueous solution is cooled from 170° to 80° C. in the third to seventh crystallizers.

11. The process according to claim 1, wherein steam generated by pressure release cooling of a crystallizer for the first crystallization zone, is used as a heating energy for dissolving the crude terephthalic acid slurry.

12. The process according to claim 1, wherein terephthalic acid particles are obtained wherein the proportion of particles having particle sizes exceeding 210 μm is at most 7 wt %.

13. The process according to claim 1, wherein terephthalic acid particles are obtained which have a mean particle diameter of from 50 to 150 μm.

14. The process according to claim 1, wherein terephthalic acid particles are obtained wherein the proportion of bulky particles having particle sizes exceeding 2.0 mm is at most 0.5 ppm.

15. The process according to claim 1, wherein terephthalic acid particles are obtained in which the proportion of bulky particles having particle sizes exceeding 1.0 mm is at most 20 ppm.

16. The process according to claim 14, wherein the bulky particles of terephthalic acid are removed by a sieve.

17. The process according to claim 15, wherein the bulky particles of terephthalic acid are removed by a sieve.

* * * * *

UNITED STATES PATENT AND TRADEMARK OFFICE
CERTIFICATE OF CORRECTION

PATENT NO. : 5,567,842
DATED : OCTOBER 22, 1996
INVENTOR(S) : Yoshiaki IZUMISAWA et al It is certified that error appears in the above-identified patent and that said Letters Patent is hereby corrected as shown below:

Column 9, last line, "kg/m$^3$" should read --kw/m$^3$--.

Column 11, Table 2, the heading in the last column, "Comp. Ex. 6" should read -- Comp. Ex. 7--

Column 11, line 65, "stirring vanes", should read --impeller--.

Signed and Sealed this

Eighth Day of June, 1999

Q. TODD DICKINSON

*Attest:*

*Attesting Officer*   Acting Commissioner of Patents and Trademarks